United States Patent [19]

Becker et al.

[11] 4,110,461

[45] Aug. 29, 1978

[54] EFFECT OF DIPHENYLHYDANTOIN AND RELATED COMPOUNDS ON GLAUCOMA

[75] Inventors: Bernard Becker; Robert L. Stamper, both of St. Louis, Mo.; Carl F. Asseff, Cleveland, Ohio; Steven M. Podos, St. Louis, Mo.

[73] Assignee: The United States of America as represented by the Department of Health, Education and Welfare, Washington, D.C.

[21] Appl. No.: 342,703

[22] Filed: Mar. 19, 1973

[51] Int. Cl.² ............................................. A61K 31/415
[52] U.S. Cl. .................................................. 424/273 R
[58] Field of Search ........................................ 424/273

[56] References Cited

PUBLICATIONS

Physicians Desk Reference, PDR, (1971) 25th Edition, p. 1003.
Cutting, Handbook of Pharmacology, 1969, pp. 669–671.
Becker et al., J. Clin. Endocrinol. Metab., vol. 32, No. 5, pp. 669–670 (1971).

*Primary Examiner*—Leonard Schenkman
*Attorney, Agent, or Firm*—John S. Roberts, Jr.; Norman J. Latker; Thomas G. Ferris

[57] ABSTRACT

A therapeutic method of alleviating the symptoms and relieving intraocular pressure associated with open or wide-angle glaucoma which comprises administering a compound selected from diphenylhydantoin (DPH), mephenytoin, and ethotoin in an amount ranging from 200–900 mg per day preferably on a split or divided dosage basis for a period of 2–5 months. A preferred regimen for DPH is 100 mg three times per day.

2 Claims, No Drawings

EFFECT OF DIPHENYLHYDANTOIN AND RELATED COMPOUNDS ON GLAUCOMA

The present invention relates to certain novel treating agents which are used therapeutically in humans to alleviate some of the symptoms of glaucoma. The present invention has been reported in part in a paper authored by the same inventors entitled Effect of Diphenylhydantoin on Glaucomatous Field Loss: A Preliminary Report, Bernard Becker, Robert L. Stamper, Carl F. Asseff, and Steven M. Podos, published in the Transactions American Academy of Ophthalmology and Otolaryngology, March–April, 1972, pages 412–422.

Glaucoma is a disease complex characterized by intraocular tension that, if sufficiently high and persistent, leads to irreversible blindness. The prior art has shown that anti-cholinesterase (anti-ChE) drugs have been utilized in the treatment of glaucoma such as physostigmine salicylate, neostigmine bromide, demecarium bromide, etc., and particularly the anti-ChE drugs are of value in the management of primary as well as certain categories of secondary type glaucoma. Primary glaucoma is subdivided into narrow-angle (acute congestive) and wide-angle (chronic simple) types, based on the configuration of the angle of the anterior chamber where reabsorption of the aqueous humor occurs. It was found that the physostigmine anti-ChE produce a fall of intraocular tension in both types of primary glaucoma chiefly lowering the resistance of outflow of the aqueous humor.

The present invention is directed towards therapeutic treatment of wide-angle or otherwise known as open-angle glaucoma, and in this illness the mechanism of the improvement in aqueous outflow is not entirely clear, but it is theorized that the ciliary muscle improves reabsorption. In wide-angle glaucoma it is further noted that there is a gradual insiduous onset permitting chemotherapeutic treatment, whereas narrow-angle glaucoma has usually been treated surgically. In treating the present illness, chronic simple glaucoma (wide or open-angle), therapy is designed to utilize the lowest concentration of drug at the longest interval between dosages. The known anti-ChE agents used as preferred are physostigmine salicylate and demecarium bromide. A discussion of glaucoma generally is set out in Goodman and Gilman, The Pharmacological Basis of Therapeutics, Fourth Edition, 1970, pages 458–460, and Third Edition, 1966, pages 458-459.

In general, when applied locally to the conjunctiva, anti-ChE agents cause pupillary constriction and other secondary changes. The miosis which occurs causes the intraocular pressure to fall and thus relieves the basic symptom of glaucoma. Diphenylhydantoin USP and diphenylhydantoin sodium USP (Dilantin), together with such closely structured and analogous drugs such as mephenytoin (Mesantoin) and ethotoin (Peganone) were originally proposed clinically for use as anticonvulsant compounds for adjective treatment in electroshock therapy and in long-term alleviation of epileptic seizures. A useful report of hydantoins as anticonvulsants is in Krantz and Carr, Pharmacologic Principles of Medical Practice, 8th Edition, Williams and Wilkins, 1972, pages 154–159.

The compound of choice (DPH) is as follows:

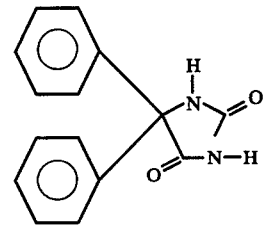

The pharmacologic agents of the present invention are utilized to reverse the pathogenic mechanism of field loss in glaucoma in open-angle glaucoma. The operable dosage regimen is as follows:

| Generic Name | Selected Trade Name | Range of Oral Dose Daily in Divided Doses |
|---|---|---|
| Diphenylhydantoin | Dilantin | 300–900 mg |
| Mephenyltoin | Mesantoin | 200–600 mg |
| Ethotoin | Peganone | 200–300 mg |

A divided or split dosage per day is recommended and an optimum dosage for DPH is 100 mg three times a day for a period of 2–5 months.

The therapeutic evidence points to ischemia of the optic nerve as a major factor in glaucoma and the present therapy is apparently directed towards the repair of cell bodies in the optic nerve when the damage by the ischemic process is not yet irreversibly altered.

EXAMPLE

In an open experiment involving 21 patients with open or wide-angle glaucoma, 17 patients were treated for 2 or more months with diphenylhydantoin (DPH) and 7 of the 17 (41%) showed definite improvements in their visual fields; 4 demonstrated no change in their fields despite maintenance of intraocular pressures that previously had been associated with rapid progression of field loss; and the remaining 6 patients showed no change when DPH was added and they had stabilized, controlled intraocular pressures. Progression of visual field loss did not occur in any of the 17 patients while on DPH therapy.

Four of the 21 patients showed return of previous visual field loss within 2–3 months after discontinuing the DPH therapy. In 2 of these patients who tolerated DPH, improvement of the visual field was again demonstrated when the drug was restarted. The remaining two could not be re-treated because of side effects. Field loss was tested by kinetic and static perimetry using the method of Goldmann, Opthalmologica 130:357-377, 1955.

The embodiments of this invention in which an exclusive property or privilege is claimed are defined as follows:

1. A method of alleviating visual field loss associated with open-angle glaucoma in humans which comprises orally treating said humans suffering from glaucoma with diphenylhydantoin (DPH) administered in an oral daily dose of 200–900 mg in divided doses for 2-5 months.

2. The method according to claim 1 wherein the oral daily dosage is 300 mg in divided doses.